United States Patent [19]

Burton

[11] Patent Number: 4,842,932

[45] Date of Patent: Jun. 27, 1989

[54] FIBER-CONTAINING YARN POSSESSING ANTIMICROBIAL ACTIVITY

[75] Inventor: Wendel L. Burton, Arden, N.C.

[73] Assignee: BASF Corporation, Williamsburg, Va.

[21] Appl. No.: 165,645

[22] Filed: Mar. 8, 1988

[51] Int. Cl.$^4$ ............... B32B 27/18; D02G 3/04; D03D 27/00

[52] U.S. Cl. .................................. 428/375; 8/490; 428/97; 428/378; 428/389; 428/394; 428/395; 428/396; 428/907

[58] Field of Search ............... 428/375, 378, 379, 389, 428/394, 395, 396, 907, 97; 106/15.08, 18.31; 8/490

[56] References Cited

U.S. PATENT DOCUMENTS

| | | | |
|---|---|---|---|
| 3,296,000 | 1/1967 | Bockno et al. | 106/18.31 |
| 3,877,965 | 4/1975 | Broadbent et al. | 427/304 |
| 3,959,556 | 5/1976 | Morrison | 428/364 |
| 4,608,289 | 8/1986 | McIntosh | 428/97 |
| 4,624,677 | 11/1986 | Guilbault et al. | 428/361 |
| 4,624,679 | 11/1986 | McEntee | 8/650 |
| 4,643,920 | 2/1987 | McEntee et al. | 428/379 |
| 4,647,601 | 3/1987 | McIntosh | 523/122 |
| 4,649,078 | 3/1987 | McEntee et al. | 428/375 |
| 4,649,079 | 3/1987 | Guilbault et al. | 428/375 |

*Primary Examiner*—James C. Cannon
*Attorney, Agent, or Firm*—Edward F. Sherer

[57] ABSTRACT

A yarn having antimicrobial properties comprising a plurality of individual synthetic polymer filaments wherein at least one of the filaments but less than 20% of the total of the individual filaments in the yarn has a sufficient amount of antimicrobial activity to inhibit microbial growth in the entire yarn.

33 Claims, 1 Drawing Sheet

FIGURE
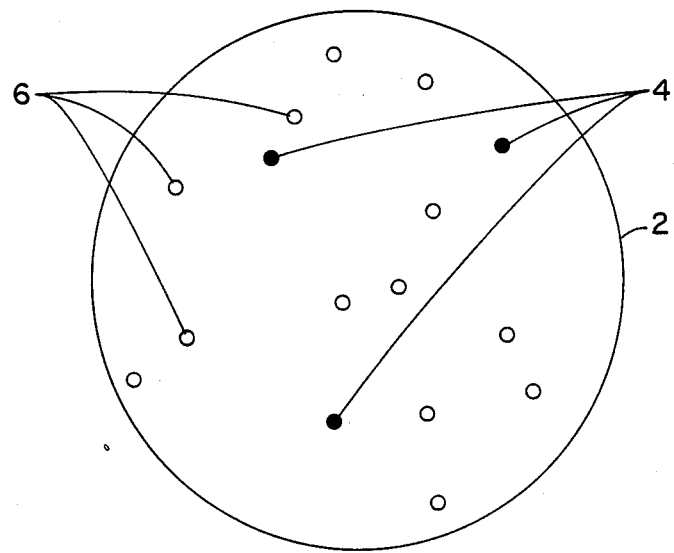

FIBER-CONTAINING YARN POSSESSING ANTIMICROBIAL ACTIVITY

I. FIELD OF THE INVENTION

The present invention relates to synthetic polymer articles composed of fibers, filaments, and yarns, such as fabrics, carpets, and the like which possess antimicrobial activity.

II. DESCRIPTION OF THE PRIOR ART

In the past, it has been known that various compounds which are known as antimicrobial agents can be applied either to the surface of fibers or impregnated therein to provide the fibers antimicrobial activity, i.e., activity against bacterial growth and also antimycotic activity, i.e., activity against rotting and fungal attack. In general, fibers treated in this manner are not effective over protracted periods of time because the antimicrobial agents retain effective antimicrobial activity for only short periods of time. One or two washings of the fibers, exposure of the fibers to ultraviolet light and other light radiation, or traffic on the surface of the fibers when they are used in carpets severely diminishes or destroys the effectiveness of the fibers for inhibiting the growth of microorganisms.

The term "antimicrobial agent" as used herein is intended to mean that such agent has the capacity to either prevent, destroy, inhibit, or combinations thereof, the growth of bacteria, fungi, molds, and other microorganisms. The terms "Gram-positive" and "Gram-negative" refer to Gram's method for segregating microorganisms based on fundamental biological differences between the two types of bacteria. In general, the procedure consists of staining a fixed bacteria smear with gentian violet solution containing a small quantity of aniline, washing this off with water, and flooding with Lugol's iodine solution. The iodine solution is washed off after a time and the smear decolorized with alcohol, acetone, acetone and ether, or some other agent and counterstained with a dye of contrasting color, such as saframine O or Bismarck brown. By this means, bacteria may be divided into two groups. Those which retain the original gentian violet in spite of the decolorization and appear dark purple on a background of the counterstain are spoken of as Gram-positive bacteria, and those which are decolorized and are colored by the counterstain are referred to as Gram-negative bacteria. The term "traffic" as used herein means the occurrence of an object, such as an individual, contacting the fibers, such as by walking or otherwise contacting a carpet composed of the fibers. The term "fiber" as used herein includes fibers of extreme or indefinite length (i.e., filaments) and fibers or short length (i.e., staple). The term yarn, as used herein, means a continuous strand of fibers.

In an attempt to overcome these problems, antimicrobial agents and, optionally, stabilizers for the agents, have been incorporated with the synthetic polymers prior to extruding the polymers into fibers. While the use of this procedure has been partially successful, certain problems remain. For instance, the resulting fibers still rapidly lose their antimicrobial activity because of abrading, ultraviolet light, heat, and during the processing, i.e., scouring, dyeing, etc., of the fibers into their final product, i.e., carpets. When increased amounts of antimicrobial agents are incorporated into the fibers to compensate for these losses, the fibers can become uneconomical because of additional expenses incurred from the increased amounts of the antimicrobial agents.

The present invention provides a yarn comprised of individual synthetic polymer fibers possessing antimicrobial activity which overcomes or at least mitigates the above described problems.

SUMMARY OF THE INVENTION

The surprising discovery has been made concerning a yarn having antimicrobial activities which comprises a plurality of individual synthetic polymer fibers, preferably in substantial parallel relationship to each other, wherein at least one of said fibers but less than 20% of the total number of fibers has a sufficient amount of antimicrobial activity to inhibit microbial growth in the entire yarn. The amount of antimicrobial activity present in the yarn is preferably an amount sufficient such that the yarn exhibits a zone of microbial inhibition in an amount of at least 1 millimeter. The yarns of the present invention prevent or inhibit the growth of both Gram-positive and Gram-negative organisms.

The term "zone of microbial inhibition" or "zone of inhibition" as used herein means a region where growth and reproduction of viable microorganisms within the zone is halted. The term "microbial inhibition" as used herein means the prevention of growth and/or reproduction of viable microorganisms.

Surprisingly, the yarns of the present invention inhibit microbial growth, although reduced amounts of antimicrobial agent are required. In addition, the yarns maintain their antimicrobial activity over extended periods of time.

BRIEF DESCRIPTION OF THE DRAWING

The FIGURE is a cross-sectional view illustrating the individual filaments of the yarn.

DESCRIPTION OF THE PREFERRED EMBODIMENTS

Antimicrobial agents suitable for use in the present invention are those agents which provide microbial inhibition when present in at least one fiber of the yarn bundle. Examples of such antimicrobial agents include antimicrobial bisphenoxarsines and bisphenarsazines compounds including compounds represented by the following formula:

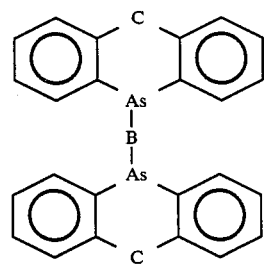

I wherein:
  C is selected from the group consisting of oxygen and NH; and,
  B is selected from the group consisting of oxygen and sulfur.

Examples of such compounds corresponding to the above formula I include 10,10'-oxybisphenoxarsine (OBPA); 10,10'-oxybisphenarazine; 10,10'-thiobisphenarsazine; 10,10'-thiobisphenoxarsine; and mixtures thereof.

Another class of antimicrobial agents suitable for use in the present invention include oxidatively stable and non-toxic metal powders, such as silver and platinum, which are capable of imparting antimicrobial activity to fibers comprising synthetic polymers. When such metals are deposited on the surface of the fibers, the fibers exhibit excellent antimicrobial activity. Procedures for depositing or plating of the metal powders on the surface of the fibers are known to persons skilled in the art. A particularly preferred procedure for depositing silver powder on the surface of a fiber is disclosed in U.S. Pat. No. 3,877,965, which is hereby incorporated by reference. The amount of metal powder utilized will depend on a number of factors. Thus, there are no set parameters in this regard. Excellent antimicrobial activity can be achieved in a yarn utilizing fibers coated with about 0.75 to about 14% by weight metal, preferably silver, based on the total weight of the antimicrobial fibers. The resulting antimicrobial yarn preferably contains from about 0.03 to about 0.1% by weight metal based on the total weight of the yarn.

Still another class of antimicrobial agents suitable for use in the present invention is alkyl phosphate derivatives represented by the following formula:

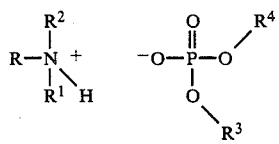

wherein
R is an alkyl group containing from about 8 to about 18 carbon atoms;
$R^1$ and $R^2$ are the same and are selected from the group consisting of an alkyl group containing from about 1 to about 14 carbon atoms and a hydroxy alkyl containing from about 1 to about 18 carbon atoms; and,
$R^3$ and $R^4$ are independently selected from the group consisting of hydrogen and an alkyl group containing from about 1 to about 18 carbon atoms and at least one of $R^3$ and $R^4$ is an alkyl group.

Examples of groups corresponding to R include straight chain or branched alkyl groups such as n-octyl, 2-methylheptyl, n-nonyl, 4-methyloctyl, n-nonyl, 2,2-dimethylheptyl, n-decyl, 2-methylnonyl, n-undecyl, 2,2-dimethylnonyl, n-dodecyl, n-tudecyl, and n-tetradecyl, n-pentadecyl, n-hexadecyl, n-heptadecyl, n-octadecyl, 2-methyloctyl, 3-ethylnonyl, and the like.

Examples of groups corresponding to $R^1$ and $R^2$ include straight chain and branched alkyl groups such as methyl, ethyl, n-propyl, isopropyl, n-butyl, isobutyl, tert-butyl, n-pentyl, isopentyl, n-hexyl, 2-methylpentyl, n-heptyl, 2,3-dimethylpentyl, 2-methylhexyl, n-octyl, 2-methylheptyl, n-nonyl, 4-methyloctyl, n-nonyl, 2,2-dimethylheptyl, n-decyl, 2-methylnonyl, n-undecyl, 2,2-dimethylnonyl, n-dodecyl, n-tridecyl, and n-tetradecyl and corresponding hydroxy alkyl groups such as hydroxymethyl, hydroxyethyl, 1-hydroxypropyl, 2-hydroxy-2-methylpropyl, 1-hydroxybutyl, 2-hydroxypentyl, 2-hydroxyhexyl, 1-hydroxyheptyl, 2-hydroxy-2-methylheptyl, 1-hydroxynonyl, 1-hydroxydecyl, 1-hydroxyundecyl, 1-hydroxydodecyl, 1-hydroxytridecyl, 1-hydroxytetradecyl, and the like.

Examples of alkyl groups corresponding to $R^3$ and $R^4$ include straight chain and branched alkyl groups such as methyl, ethyl, n-propyl, isopropyl, n-butyl, isobutyl, tert-butyl, n-pentyl, isopentyl, n-hexyl, 2-methylpentyl, n-heptyl, 2,3-dimethylpentyl, 2-methylhexyl, n-octyl, 2-methylheptyl, n-nonyl, 4-methyloctyl, n-nonyl, 2,2-dimethylheptyl, n-decyl, 2-methylnonyl, n-undecyl, 2,2-dimethylnonyl, n-dodecyl, n-tridecyl, n-tetradecyl, n-pentadecyl, n-hexadecyl, n-heptadecyl, and n-octadecyl.

The alkyl phosphate derivatives can be either monoester derivatives, diester derivatives, or mixtures thereof. The preparation of these compounds is disclosed in U.S. Pat. Nos. 4,608,289 and 4,647,601, which are hereby incorporated by reference.

Examples of suitable alkyl phosphate derivatives include monoester derivatives such as dodecyl bis(hydroxyethyl)octyl ammonium phosphate, dodecyl bis(hydroxyethyl)ethyl ammonium phosphate, octyl bis(hydroxyethyl)ethyl ammonium phosphate and mixtures thereof and diester products such as dodecyl bis(hydroxyethyl) di-octyl ammonium phosphate, dodecyl bis(hydroxyethyl) di-ethyl ammonium phosphate, dodecyl bis(hydroxyethyl) di-propyl ammonium phosphate, octyl bis(hydroxyethyl) di-ethyl ammonium phosphate and mixtures thereof.

Examples of fiber-forming synthetic polymers suitable for use in the invention include synthetic thermoplastic polymers which are capable of being formed into fibers such as by melt extrusion including polyolefins, for example, homopolymers of olefins such as low-density polyethylene, high-density polyethylene, polypropylene, and the like, and copolymers of olefins with other ethylenically unsaturated monomers such as ethylene-propylene copolymer, and an ethylenebutene copolymer.

Polyamides find particular application in the present invention. Examples of such polyamides include homopolyamides and copolyamides which are obtained by the polymerization of lactam or aminocaprionic acid or a copolymerization product of a diamine and a dicarboxylic acid.

Typical polyamides include nylon 6, nylon 6/6, nylon 6/10, nylon 6/12, nylon 11, nylon 12, and copolymers thereof or mixtures thereof. Polyamides can be also copolymers of nylon 6 or nylon 6,6 and a nylon salt obtained by reacting a dicarboxylic acid component such as terephthalic acid, isophthalic acid, adipic acid and sebacic acid with a diamine such as hexamethylenediamine, methaxylenediamine, and 1,4-bisaminomethylcyclohexane.

Polyester also finds particular application in the present invention. The preferred polyesters are the linear terephthalate polyesters, i.e., polyesters of a glycol containing from 2 to 20 carbon atoms and a dicarboxylic acid component comprising at least about 75% terephthalic acid. The remainder, if any, of the dicarboxylic acid component may be any suitable dicarboxylic acid such as sebacic acid, adipic acid, isophthalic acid, sulfonyl-1,4-4-dibenzoic acid, or 2,8-di-benzofurandicarboxylic acid. The glycols may contain more than two carbon atoms in the chain, e.g., diethylene glycol, butylene glycol, decamethylene glycol, and bis-1,4-(hydroxymethyl)cyclohexane. Examples of linear terephthalate polyesters which may be employed include poly(ethylene terephthalate), poly(butylene terephthalate), poly(ethylene terephthalate/5-chloroisophthalate), include poly(ethylene terephthalate), poly(butylene terephthalate), poly(ethylene terephthalate/5-chloroisophthalate), poly(ethylene terephthalate/5-[sodium sulfo]-isophthalate), poly(cyclohexane-1,4-dimethylene terephthalate/hexahydroterephthalate).

Referring now more particularly to the FIGURE, a cross sectional view of a multifilament yarn (2), which is sometimes referred to as a tow or bundle, is generally illustrated.

Intermingled or interwoven in the yarn (2) are one or more individual filaments having antimicrobial properties (4) with individual filaments not having antimicrobial properties (6). In the FIGURE, the yarn (2) is shown with three filaments having antimicrobial properties (4) for the purpose of illustration. However, the number of individual filaments on the yarn having antimicrobial properties and not having antimicrobial properties is in no way limited by the FIGURE. In addition, the filaments having antimicrobial properties can be randomly positioned in the yarn or, alternatively, can be placed in the yarn at predetermined positions, i.e., close to the outer surface of the yarn, in the center of the yarn, at predetermined relative positions to one another, etc. Typically, a multifilament yarn will contain from about 14 to about 300 filaments, and, more preferably, from about 96 to about 230 filaments having a denier/filament preferably in the range of from about 2 to about 28, and more preferably, from about 11 to about 22. The amount or number of fibers having antimicrobial properties utilized in the yarn will depend upon variables such as denier and amount of antimicrobial agent present in the antimicrobial fibers. At least one of the antimicrobial filaments must be present in the yarn and, to achieve the advantages of the present invention, the yarn will not contain more than 20% fibers having antimicrobial properties based on the total number of filaments in the yarn.

Preferably, the number of antimicrobial filaments to the number of total filaments in the yarn is in a ratio in the range of from about 1:250 to about 1:4, and, more preferably, from about 1:200 to about 1:20. In addition, the antimicrobial fibers and fibers not possessing antimicrobial properties do not have to have the same denier; however, in certain applications, yarns having fibers of similar denier are preferred.

Generally, however, at least 0.2 to about 20.0 weight percent based on the total weight of the yarn should be composed of fibers having antimicrobial properties and, more preferably at least 0.4 to about 5.0 weight percent based on the total weight of the yarn should be composed of fibers having antimicrobial properties.

Preferably, the individual antimicrobial filaments will contain a sufficient amount of antimicrobial agent such that active antimicrobial agent is present in the entire filament bundle in an amount in the range of from about 15 ppm to about 600 ppm, and, more preferably, from about 50 to about 500 ppm. Antimicrobial activity of the fibers can be outside of this range, but antimicrobial activity is maintained in the yarn for a longer period of time if amounts within this range are utilized. If lesser amounts of antimicrobial agents are utilized, i.e., 30 ppm, the antimicrobial activity of the yarn rapidly dissipates. Amounts of 50 ppm or more allows the yarn to maintain its antimicrobial activity for larger periods of time. As previously stated, prior art yarns have been used in the past in which all filaments contain the same amount of antimicrobial agent. The yarns of the present invention are more economic, as not every filament in the yarn needs to have antimicrobial activity. Instead, a small number of filaments in the yarn possess antimicrobial activity, yet the yarn itself surprisingly exhibits antimicrobial activity.

In the particularly preferred embodiments, the yarn will contain more than 0.001 but less than 5.0% by weight antimicrobial agent based on the total weight of the yarn and, more preferably, about 0.002 to about 0.050% by weight antimicrobial agent based on the total weight of the yarn.

In the most preferred embodiments, the antimicrobial yarns will have a zone of inhibition of at least 1 millimeter. Zones of inhibition of at least 2 millimeters are considered excellent.

Although, as previously stated, the number of antimicrobial fibers, the total number of filaments in the yarn, and denier of the filaments is not subject to any limitations except that the yarn must exhibit antimicrobial activity, Table I represents examples of yarns that find particular application in the invention.

TABLE I

| Yarn Designation | Antimicrobial Filaments | | | | Nontreated Filaments | | | | Total Denier of Yarn (grams) | Wt. % Antimicrobial Agent/ Total Wt. Yarn |
|---|---|---|---|---|---|---|---|---|---|---|
| | Polymer | No. | Total Denier (grams) | Amount of Antimicrobial Agent/Filament (ppm) | Polymer | No. | Denier (grams) | Total Denier of Filaments (grams) | | |
| A | Nylon 6 | 1 | 20 | 5,000 | Nylon 6 | 224 | 19.64 | 4,400 | 4,420 | 0.0023 |
| B | Nylon 6 | 8 | 90 | 10,000 | Nylon 6 | 224 | 19.64 | 4,400 | 4,480 | 0.020 |
| C | Nylon 6 | 7 | 21 | 120,000 | Nylon 6 | 224 | 19.64 | 4,400 | 4,411 | 0.0570 |
| D | Nylon 6 | 3 | 21 | 15,000 | Polyester | 224 | 18.00 | 4,000 | 4,021 | 0.0078 |
| E | Polyolefin | 20 | 130 | 3,000 | Nylon 6 | 224 | 16.00 | 3,600 | 3,730 | 0.0105 |

The preparation of the yarns of the present invention is known to persons skilled in the art. One such procedure involves preparing fibers having antimicrobial activity by melt spinning the fibers with antimicrobial agents or coating the fiber with antimicrobial agents and fibers without antimicrobial activity using procedures known to persons skilled in the art and combining the desired number of each type of fiber to produce antimicrobial yarn having antimicrobial activity.

The yarns find particular application in textile articles, fabrics, carpets, and the like. The yarns find particular applications in the tufts of a carpet, especially produces colored carpets where the influence of antimicrobial color can be minimized.

The invention is further exemplified by the examples below which are presented to illustrate certain specific embodiments of the invention, but are not intended to be construed so as to be restrictive of the scope and spirit thereof.

EXAMPLE

A number of carpet tufts were prepared. The designation of the tufts and their components are set forth below in Table II:

TABLE II

| Sample | Components |
|---|---|
| A | A tuft having a total denier of 4400 and comprising 8 nylon plies, each filament of the plies meltspun with OBPA. |
| B | A total of 8 nylon filaments having a total denier of 90, each filament meltspun with OBPA and a stabilizer, commingled with 8 nylon plies, 550 denier per ply, to produce a tuft having a total denier of 4490. |
| C | A total of 8 polypropylene filaments having a total denier of 62, each filament meltspun with OBPA and a stabilizer, commingled with 8 nylon plies, 550 denier per ply, to produce a tuft having a total denier of 4462. |
| D | A total of 8 polypropylene filaments having a total denier of 53, each filament coated with OBPA and a stabilizer commingled with 8 nylon plies, 550 denier per ply, to produce a tuft having a total denier of 4453. |
| E | A total of 8 nylon filaments having a total denier of 68, each filament coated with OBPA and a stabilizer commingled with 8 nylon plies, 550 denier per ply, to produce a tuft having a total denier of 4468. |
| F | A total of 7 nylon filaments having a total denier of 20 and being coated with 12 percent by weight silver based on the weight of the filament commingled with 8 nylon plies, 550 denier per ply, to produce a tuft having a total denier of 4420. |
| G | Tufts identical to sample F arranged with tufts not containing antimicrobial agents, having a total denier of 4400 and comprising 8 nylon plies, 550 denier per ply. The arrangement produced a configuration such that every fourth row of tuft comprised sample F and the 3 other rows comprised the tuft without any antimicrobial agents. |

In order to determine the antimicrobial effectiveness of above-designated tufts on test organisms, tests were performed which comprised the following important steps:

1. Petri dishes were prepared by adding nutrient agar to sterile petri dishes.
2. Each of the tufts set forth in Table II was cut into ¾ inch diameter circle and each sample was placed separately into the prepared petri dishes.
3. Additional agar was slowly added to each petri dish in an amount such that the samples were covered to a depth of about 2 millimeters.
4. Each sample was then inoculated with either *Staphylococcus aureus* which is representative of a gram-positive bacteria, or *Klebsiella pneumoniae* which is representative of a gram-negative bacteria, and placed in incubation at a temperature of 37° C. for a period of time of 24 hours.
5. After the 24 hour incubation period, the samples were visually checked for either the growth of bacteria or a clear zone of growth inhibition around the samples. The zone of growth inhibition was measured in millimeters.

The amount of OBPA present in the fibers was determined by measuring the area under the liquid chromatographic peak for the OBPA (standardized) against known pure samples. The same procedure applied to measuring of the major decomposition product of OBPA (phenoxyarsenic acid—PAA). The carpets were subject to overnight soxhlet extractions to remove the OBPA. A backup analysis was also carried out to measure total arsenic content by the Atomic Absorption method where the total amounts represent the sum of OBPA and PAA.

A comparison was made between OBPA (theoretical) and OBPA (actual) in order to determine the amount of OBPA degradation during the processing of the fibers.

The results of these tests are reported in Table III.

TABLE III

| SAMPLE | OBPA - THEORETICAL (amount added) in entire bundle - ppm | OBPA (amount measured ppm) | PPA (amount measured ppm) | BIOLOGICAL ACTIVITY STAPHYLOCCUS ZONE OF INHIBITION (mm) | KLEBSIELLA ZONE OF INHIBITION (mm) |
|---|---|---|---|---|---|
| A | 300–500 | 59 | 295 | 8 | 2 |
| B | 100 | 41 | 27 | 6 | 1 |
| C | 67 | 15 | 22 | 6 | ½ |
| D | 12 | 6 | 7 | 3 | 0 |
| E | 15 | 6 | 7 | 0 | 0 |
| F | Not Applicable (N/A) | N/A | N/A | 2 | ½ |
| G | N/A | N/A | N/A | 1 | 0 |

The results of the tests demonstrate the effectiveness of the present invention against both Gram-positive (*Staphylococcus aureus*) and Gram-negative (*Klebsiella pneumoniae*) organisms. Furthermore, less relative degradation of OBPA occurred with the yarn of the present invention than prior art yarns, i.e., Sample A (prior art) versus Samples B through D. Sample E demonstrates that a sufficient amount of antimicrobial agent must be present in the antimicrobial fiber of the yarn to inhibit bacteria growth. Otherwise, the yarn will not be protected.

This invention is not limited to the above-described specific embodiments thereof; it must be understood, therefore, that the detail involved in the descriptions of the specific embodiments is presented for the purpose of illustration only, and reasonable variations and modifications, which will be apparent to those skilled in the art, can be made in this invention without departing from the spirit and scope thereof.

What is claimed is:

1. A yarn having antimicrobial properties containing a mixture of individual filaments comprising a fiber-forming synthetic polymer wherein at least one of said individual filaments but less than 20% of the total number of said individual filaments has an effective amount of an antimicrobial agent to inhibit microbial growth on the entire yarn.

2. The yarn recited in claim 1 wherein said antimicrobial agent is selected from the group consisting of
   (a) bisphenoxarsines and bisphenarsazines represented by the following formula:

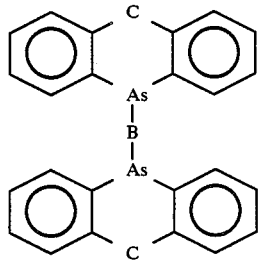

wherein:

C is selected from the group consisting of oxygen and NH; and,

B is selected from the group consisting of oxygen and sulfur;

(b) alkyl phosphate derivatives represented by the following formula:

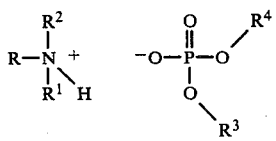

wherein

R is an alkyl group containing from about 8 to about 18 carbon atoms;

$R^1$ and $R^2$ are the same and are selected from the group consisting of an alkyl group containing from about 1 to about 14 carbon atoms and a hydroxy alkyl containing from about 1 to about 18 carbon atoms; and, $R^3$ and $R^4$ are independently selected from the group consisting of hydrogen and an alkyl group containing from about 1 to about 18 carbon atoms and at least one of $R^3$ and $R^4$ is said alkyl group; and (c) an oxidatively stable and non-toxic metal powder selected from the group consisting of silver and platinum.

3. The yarn recited in claim 2 wherein said synthetic polymers are selected from the group consisting of polyolefins, polyamides, polyesters, and mixtures thereof.

4. The yarn recited in claim 3 wherein R is selected from the group consisting of n-octyl, 2-methylheptyl, n-nonyl, 4-methyloctyl, n-nonyl, 2,2-dimethylheptyl, n-decyl, 2-methylnonyl, n-undecyl, 2,2-dimethylnonyl, n-dodecyl, n-tridecyl, n-tetradecyl, n-pentadecyl, n-hexadecyl, n-heptadecyl, n-octadecyl, 2-methyloctyl, and 3-ethylnonyl.

5. The yarn recited in claim 4 wherein $R^1$ and $R^2$ are independently selected from the group consisting of methyl, ethyl, n-propyl, isopropyl, n-butyl, isobutyl, tert-butyl, n-pentane, isopentyl, n-hexyl, 2-methylpentyl, n-heptyl, 2,3-dimethylpentyl, 2-methylhexyl, n-octyl, 2-methylheptyl, n-nonyl, 4-methyloctyl, n-nonyl, 2,2-dimethylheptyl, n-decyl, 2-methylnonyl, n-undecyl, 2,2-dimethylnonyl, n-dodecyl, n-tridecyl, n-tetradecyl, hydroxymethyl, hydroxyethyl, 1-hydroxypropyl, 2-hydroxy-2-methylpropyl, 1-hydroxybutyl, 2-hydroxypentyl, 2-hydroxyhexyl, 1-hydroxyheptyl, 2-hydroxy-2-methylheptyl, 1-hydroxynonyl, 1-hydroxydecyl, 1-hydroxyundecyl, 1-hydroxydodecyl, 1-hydroxytridecyl, and 1-hydroxytetradecyl.

6. The yarn recited in claim 5 wherein $R^3$ and $R^4$ are independently selected from the group consisting of hydrogen, methyl, ethyl, n-propyl, isopropyl, n-butyl, isobutyl, tert-butyl, n-pentyl, isopentyl, n-hexyl, 2-methylpentyl, n-heptyl, 2,3-dimethylpentyl, 2-methylhexyl, n-octyl, 2-methylheptyl, n-nonyl, 4-methyloctyl, n-nonyl, 2,2-dimethylheptyl, n-decyl, 2-methylnonyl, n-undecyl, 2,2-dimethylnonyl, n-dodecyl, n-tridecyl, n-tetradecyl, n-pentadecyl, n-hexadecyl, n-heptadecyl, and n-octadecyl.

7. The yarn recited in claim 6 wherein said bisphenoxarsines and said bisphenarsazines are selected from the group consisting of 10,10'-oxybisphenoxarsine; 10,10'-oxybisphenarazine; 10,10'-thiobisphenarsazines; 10,10'-thiobisphenoxarsine; and mixtures thereof.

8. The yarn recited in claim 7 wherein said alkylphosphate derivatives are selected from the group consisting of dodecyl bis(hydroxyethyl)octyl ammonium phosphate, dodecyl bis(hydroxyethyl)ethyl ammonium phosphate, octyl bis(hydroxyethyl)ethyl ammonium phosphate, dodecyl bis(hydroxyethyl) di-octyl ammonium phosphate, dodecyl bis(hydroxyethyl) di-ethyl ammonium phosphate, dodecyl bis(hydroxyethyl) di-propyl ammonium phosphate, octyl bis(hydroxyethyl) di-ethyl ammonium phosphate and mixtures thereof.

9. The yarn recited in claim 8 wherein said metal powder is silver powder.

10. The yarn recited in claim 9 wherein said mixture of individual filaments comprises from about 14 to about 300 filaments.

11. The yarn recited in claim 10 wherein the ratio of number of antimicrobial filaments to number of total filaments in said yarn is in the range of from about 1:200 to about 1:20.

12. The yarn recited in claim 11 wherein each of said individual filaments has a denier in the range of from about 11 to about 22.

13. The yarn recited in claim 12 wherein said filaments having antimicrobial properties are present in said yarn in an amount in the range of from about 0.002 to about 0.05 weight percent based on the total weight of said yarn.

14. The yarn recited in claim 13 wherein said antimicrobial agent is 10,10'-oxybisphenoxarsine and is present in said yarn in an amount in the range of from about 50 to about 500 ppm.

15. The yarn recited in claim 14 wherein said individual filaments are in substantially parallel relationship to each other.

16. The yarn recited in claim 14 wherein said individual filaments are interwoven.

17. The yarn recited in claim 14 wherein said yarn has a zone of inhibition of at least 2 mm for Staphylococcus aureus.

18. A method of preparing a yarn having a sufficient amount of antimicrobial activity to inhibit microbial growth in the yarn comprising commingling a mixture of individual filaments comprising fiber-forming synthetic polymers wherein at least one of said individual filaments but less than 20% of the total of said individual filaments has an effective amount of an antimicrobial agent to inhibit microbial growth on the entire yarn.

19. The method recited in claim 18 wherein said antimicrobial agent is selected from the group consisting of
(a) bisphenoxarsines and bisphenarsazines represented by the following formula:

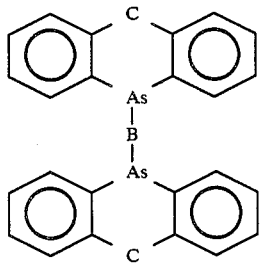

wherein:
C is selected from the group consisting of oxygen and NH; and,
B is selected from the group consisting of oxygen and sulfur;
(b) alkyl phosphate derivatives represented by the following formula:

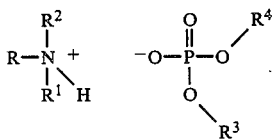

wherein
R is an alkyl group containing from about 8 to about 18 carbon atoms;
$R^1$ and $R^2$ are the same and are selected from the group consisting of an alkyl group containing from about 1 to about 14 carbon atoms and a hydroxy alkyl containing from about 1 to about 18 carbon atoms; and,
$R^3$ and $R^4$ are independently selected from the group consisting of hydrogen and an alkyl group containing from about 1 to about 18 carbon atoms and at least one of $R^3$ and $R^4$ is said alkyl group; and
(c) an oxidatively stable and non-toxic metal powder selected from the group consisting of silver and platinum.

20. The method recited in claim 19 wherein said synthetic polymers are selected from the group consisting of polyolefins, polyamides, polyesters, and mixtures thereof.

21. The method recited in claim 20 wherein n-octyl, 2-methylheptyl, n-nonyl, 4-methyloctyl, n-nonyl, 2,2-dimethylheptyl, n-decyl, 2-methylnonyl, n-undecyl, 2,2-dimethylnonyl, n-dodecyl, n-tridecyl, n-tetradecyl, n-pentadecyl, n-hexadecyl, n-heptadecyl, n-octadecyl, 2-methyloctyl, and 3-ethylnonyl.

22. The method recited in claim 21 wherein $R^1$ and $R^2$ are independently selected from the group consisting of methyl, ethyl, n-propyl, isopropyl, n-butyl, isobutyl, tert-butyl, n-pentyl, isopentyl, n-hexyl, 2-methylpentyl, n-heptyl, 2,3-dimethylpentyl, 2-methylhexyl, n-octyl, 2-methylheptyl, n-nonyl, 4-methyloctyl, n-nonyl, 2,2-dimethylheptyl, n-decyl, 2-methylnonyl, n-undecyl, 2,2-dimethylnonyl, n-dodecyl, n-tridecyl, n-tetradecyl, hydroxymethyl, hydroxyethyl, 1-hydroxypropyl, 2-hydroxy-2-methylpropyl, 1-hydroxybutyl, 2-hydroxypentyl, 2-hydroxyhexyl, 1-hydroxyheptyl, 2-hydroxy-2-methylheptyl, 1-hydroxynonyl, 1-hydroxydecyl, 1-hydroxyundecyl, 1-hydroxydodecyl, 1-hydroxytridecyl, and 1-hydroxytetradecyl.

23. The method recited in claim 22 wherein $R^3$ and $R^4$ are independently selected from the group consisting of hydrogen, methyl, ethyl, n-propyl, isopropyl, n-butyl, isobutyl, tert-butyl, n-pentyl, isopentyl, n-hexyl, 2-methylpentyl, n-heptyl, 2,3-dimethylpentyl, 2-methylhexyl, n-octyl, 2-methylheptyl, n-nonyl, 4-methyloctyl, n-nonyl, 2,2-dimethylheptyl, n-decyl, 2-methylnonyl, n-undecyl, 2,2-dimethylnonyl, n-dodecyl, n-tridecyl, n-tetradecyl, n-pentadecyl, n-hexadecyl, n-heptadecyl, and n-octadecyl.

24. The method recited in claim 23 wherein said bisphenoxarsines and said bisphenarsazines are selected from the group consisting of 10,10'-oxybisphenoxarsine; 10,10'-oxybisphenarazine; 10,10'-thiobisphenarsazine; 10,10'-thiobisphenoxarsine; and mixtures thereof.

25. The method recited in claim 24 wherein said alkylphosphate derivatives are selected from the group consisting of dedecyl bis(hydroxyethyl)octyl ammonium phosphate, dodecyl bis(hydroxyethyl)ethyl ammonium phosphate, octyl bis(hydroxyethyl)ethyl ammonium phosphate, dodecyl bis(hydroxyethyl) di-octyl ammonium phosphate, dodecyl bis(hydroxyethyl) di-ethyl ammonium phosphate, dodecyl bis(hydroxyethyl) di-propyl ammonium phosphate, octyl bis(hydroxyethyl) di-ethyl ammonium phosphate and mixtures thereof.

26. The method recited in claim 25 wherein said metal powder is silver powder.

27. The method recited in claim 26 where said mixture of individual filaments comprises from about 14 to about 300 filaments.

28. The method recited in claim 27 wherein the ratio of number of antimicrobial filaments to number of total filaments in said yarn is in the range of from about 1:200 to about 1:20.

29. The method recited in claim 28 wherein each of said individual filaments has a denier in the range of from about 11 to about 22.

30. The method recited in claim 29 wherein said filaments having antimicrobial properties are present in said yarn in an amount in the range of from about 0.002 to about 0.05 weight percent based on the total weight of said yarn.

31. The method recited in claim 30 wherein said antimicrobial agent is 10,10'-oxybisphenoxarsine and is present in said yarn in an amount in the range of from about 50 to about 500 ppm.

32. The method recited in claim 31 wherein said individual filaments are in substantially parallel relationship to each other.

33. The method recited in claim 31 wherein said individual filaments are interwoven.

* * * * *